US009239315B1

(12) United States Patent
Georgeson et al.

(10) Patent No.: US 9,239,315 B1
(45) Date of Patent: Jan. 19, 2016

(54) PATCH AND METHODS FOR MONITORING A STRUCTURE INCLUDING A PATCH

(75) Inventors: Gary E. Georgeson, Federal Way, WA (US); Richard H. Bossi, Renton, WA (US)

(73) Assignee: The Boeing Company, Chicago, IL (US)

( * ) Notice: Subject to any disclaimer, the term of this patent is extended or adjusted under 35 U.S.C. 154(b) by 277 days.

(21) Appl. No.: 12/791,362

(22) Filed: Jun. 1, 2010

(51) Int. Cl.
*G01B 5/28* (2006.01)
*G01N 29/04* (2006.01)
*G06F 11/30* (2006.01)

(52) U.S. Cl.
CPC ........ *G01N 29/04* (2013.01); *G01B 5/28* (2013.01); *G06F 11/30* (2013.01)

(58) Field of Classification Search
CPC .......... G01N 29/262; G01N 2291/106; G01N 29/341; G01N 29/348; G01N 29/069; G01N 29/07; G01N 29/343; G01N 2291/0427; G01N 2291/104; G01N 29/34; G01N 2291/044; G01N 29/04; G01B 5/28; G06F 11/30
USPC .................. 702/39, 1, 35, 36, 183, 187, 189
See application file for complete search history.

(56) References Cited

U.S. PATENT DOCUMENTS

| 7,398,698 B2 * | 7/2008 | Griess et al. ............... 73/801 |
| 7,596,470 B2 * | 9/2009 | Kim ........................ 702/183 |
| 2008/0312848 A1 | 12/2008 | Fogarty et al. |
| 2009/0048789 A1 * | 2/2009 | Yu et al. ................... 702/39 |
| 2010/0132469 A1 * | 6/2010 | Giurgiutiu et al. ........ 73/628 |

OTHER PUBLICATIONS

Victor Giurgiutiu, nano-PWAS: Structurally Integrated Thin-Film Active Sensors for Structural Health Monitoring, Jan. 5, 2009, U.S. Appl. No. 61/200,532.*
Romanoni, M. et al., *Two-Dimensional Periodic Actuators for Frequency-Based Beam Steering*, Proc. of SPIE, vol. 7295, 729526, (2009), 11 pages.

* cited by examiner

*Primary Examiner* — Alexander Satanovsky
*Assistant Examiner* — Ivan Rabovianski
(74) *Attorney, Agent, or Firm* — Alston & Bird LLP (57) ABSTRACT

A patch and associated methods for monitoring and inspecting a structure are provided in order to facilitate such inspections. The patch includes a sheet of material configured to be attached to the structure and a frequency steerable array carried by the sheet of material. The frequency steerable array includes a plurality of sources for emitting structural waves in response to an input having a variable frequency such that variations in the frequency of the input cause the structural waves emitted by the plurality of sources to be controllably steered relative to the sheet of material. Methods utilizing one or more frequency steerable arrays for monitoring and inspecting a patch-repaired structure are also provided.

19 Claims, 4 Drawing Sheets

FIG. 7

PATCH AND METHODS FOR MONITORING A STRUCTURE INCLUDING A PATCH

TECHNOLOGICAL FIELD

Embodiments of the present disclosure relate generally to structural health management and, more particularly, to a patch and methods for monitoring and inspecting a structure.

BACKGROUND

A variety of structures are routinely inspected to determine the health of the structure and to identify any issues that may require further inspection, maintenance or repair. For example, buildings, bridges and the like may be regularly inspected to identify the onset of any issues that may potentially weaken or otherwise eventually render the structure unsuitable for its intended use. Similarly, vehicles, such as airplanes, trains, ships and the like, may be regularly inspected in order to identify any issues that merit further inspection, maintenance or repair.

In instances in which the inspection of a structure determines that the structure should undergo maintenance or repair, such as to address a structural anomaly identified during the inspection, the maintenance activities or other repairs are desirably performed in a timely manner such that the structure may be promptly returned to service. For some structures, such as metal or composite aerospace structures, patches have been developed to temporarily repair the aircraft, thereby allowing the aircraft to remain in service until a more opportune time for a more fulsome, but time-consuming repair. Temporary patches offer a number of advantages including a relatively rapid installation and a lower cost than that incurred for a permanent repair. As such, temporary patches may reduce the time that the structure must be out of service following discovery of a structural anomaly and increase the flexibility in scheduling a more permanent repair of the structure.

Temporary patches are generally inspected on a regular basis with inspections generally being conducted more frequently for the temporary patches than the underlying structure. However, inspection of these temporary patches may be burdensome, both from a scheduling and a labor standpoint. To avoid or reduce the costs associated with the inspection of temporary patches, more costly forms of temporary repair may be employed, the lifespan of the temporary patch upon the structure may be limited or the structure may be repaired more permanently. However, these alternatives for avoiding or reducing the costs associated with the inspection of temporary patches effectively reduce at least some of the benefits of utilizing such patches in the first instance.

Temporary patches may be inspected in various manners, including tap testing. In tap testing, the temporary patches are tapped and a technician listens for the resulting tone. Based upon the tone, the technician may identify any underlying structural anomalies, such as a delamination or the like. Unfortunately, some tap testing is subjective and provides no quantitative data for comparative purposes. However, mechanical tap testers exist that do record a signal and can be used to map a value as a function of position. As an alternative to tap testing, infrared thermography or ultrasonic scanning may be employed in order to non-destructively inspect a temporary patch. However, infrared thermography is generally relatively expensive, and ultrasonic scanning generally requires a significant time investment for conducting the test. Furthermore, each of these techniques for inspecting a patch generally requires a technician to regularly access the aircraft, such as via a lift, thereby adding to the time and expense of such inspections.

Another type of inspection for patches introduces structural waves, such as Lamb waves, and one or more sensors, such as piezo-electric sensors, for receiving the waves following propagation through the patch. By analyzing the signals received by the sensors, a determination may be made as to whether the portion of the patch in line between the location of the tap and the sensor is well bonded and intact or whether a structural anomaly was encountered. As a result of the multiple sensors generally included in a patch of this type, the wires required to communicate with the sensors and the hardware, e.g., multiplexor, required to facilitate such communication, the weight and the complexity of this type of patch may be increased more than is desired.

As such, it would be desirable to provide an improved technique for inspecting structures including, for example, the inspection of patches placed upon a structure.

BRIEF SUMMARY

A patch repair and associated methods for monitoring a structural repair are provided in order to facilitate such inspections. In this regard, the patch and the associated methods may facilitate the inspection of a structural repair in a manner that is more objective and less expensive and less time consuming than some conventional techniques.

In one embodiment, a patch is provided for repairing a structure. The patch consists of a sheet of material, such as a sheet of composite or metal material, configured to be attached to the structure and a frequency steerable array carried by the sheet of material, such as by a central portion of the sheet of material. For example, the frequency steerable array may be embedded within the sheet of material. The frequency steerable array includes a plurality of sources for emitting structural waves in response to an input having a variable frequency such that variations in the frequency of the input cause the structural waves emitted by the plurality of sources to be controllably steered relative to the sheet of material. For example, the frequency steerable array may be configured such that the structural waves are controllably steered in 360 degrees about the sheet of material.

The frequency steerable array may include a single steerable beam transducer having a plurality of piezo-electric transceivers. The frequency steerable array may be configured to capture the structural waves following interaction with a structural anomaly, thereby permitting the structural anomaly to be detected.

An assembly for repairing a structure is provided in accordance with another embodiment. The assembly includes a sheet of material configured to be attached to the structure and one or more frequency steerable arrays configured to be carried by the sheet of material, such as by being embedded within the sheet of material. Each frequency steerable array includes a plurality of sources for emitting structural waves in response to an input having a variable frequency such that variations in the frequency of the input cause the structural waves emitted by the plurality of sources to be controllably steered relative to the structure. For example, each frequency steerable array may be configured such that the structural waves are controllably steered in 360 degrees about the structure. The assembly of this embodiment may also include a processor configured to communicate with the one or more frequency steerable arrays and further configured to analyze a representation of the structural waves that return to the frequency steerable arrays following interaction with the structure in order to identify a structural anomaly. The processor may be configured to analyze a representation of the structural waves that return to the frequency steerable arrays to identify a characteristic, such as a shape or size, of the structural anomaly.

Each frequency steerable array may include a single steerable beam transducer having a plurality of piezo-electric transceivers. Each frequency steerable array may be configured to capture the structural waves following interaction with a structural anomaly, thereby permitting the structural anomaly to be detected.

A method is provided in accordance with another embodiment for monitoring a patch repaired structure by identifying a structural anomaly and then placing a patch repair with at least one frequency steerable array upon the structure. In this regard, the frequency steerable array includes a plurality of sources for emitting structural waves in response to an input having a variable frequency. The method of this embodiment provides the input to the sources of the frequency steerable array such that the structural waves emitted by the plurality of sources are controllably steered so as to interact with the structural anomaly. The structural waves returning following interaction with the structural anomaly are analyzed to identify a characteristic of the structural anomaly. For example, the structural waves may be analyzed in terms of amplitude, time and phase following their interaction with the structural anomaly.

In regard to the analysis of the structural waves in the patch, a baseline measurement may be initially captured. Thereafter, input may be repeatedly provided to the sources of the frequency steerable array with the resulting structural waves that return to the frequency steerable array also being analyzed on a repeated basis in order to identify structural waves that deviate from the baseline measurement.

In one embodiment, a plurality of frequency steerable arrays may be placed on relatively large patch repairs. As such, the structural waves returning to each of the plurality of frequency steerable arrays may be analyzed to identify a size or shape of the structural anomaly. In this regard, input may be provided to the sources of each of the frequency steerable arrays such that some structural waves are reflected from the structural anomaly and returned to the frequency steerable array that emitted the structural waves and other structural waves are reflected from the structural anomaly in the patch repair and directed to another frequency steerable array, different from the frequency steerable array that emitted the structural waves, thereby facilitating the identification of the size or shape of the structural anomaly.

In regard to the analysis of the structural waves, a baseline measurement may be initially captured. Thereafter, input may be repeatedly provided to the sources of the frequency steerable array with the resulting structural waves that return to the frequency steerable array also being analyzed on a repeated basis in order to identify structural waves that deviate from the baseline measurement. In one embodiment, the plurality of frequency steerable arrays may be placed such that the structural waves emitted by one frequency steerable array are received by another frequency steerable array. The method of one embodiment may also include fabricating the patch repair by providing a sheet of material and then directly writing upon the sheet of material. In one embodiment, wiring is directly written upon the sheet of material and the frequency steerable array is then attached to the sheet of material so as to be in electrical communication with the wiring. In another embodiment, the frequency steerable array itself is directly written upon the sheet of material.

In accordance with embodiments of the patch and associated methods, a structural patch repair may be monitored and inspected in an efficient, cost-effective and timely manner. However, the features, functions and advantages that have been discussed may be achieved independently in various embodiments of the present disclosure and may be combined in yet other embodiments, further details of which may be seen with reference to the following description and drawings.

BRIEF DESCRIPTION OF THE SEVERAL VIEWS OF THE DRAWING(S)

Having thus described embodiments of the present disclosure in general terms, reference will now be made to the accompanying drawings, which are not necessarily drawn to scale, and wherein:

DETAILED DESCRIPTION

Embodiments of the present disclosure now will be described more fully hereinafter with reference to the accompanying drawings, in which some, but not all embodiments are shown. Indeed, these embodiments may be embodied in many different forms and should not be construed as limited to the embodiments set forth herein; rather, these embodiments are provided so that this disclosure will satisfy applicable legal requirements. Like numbers refer to like elements throughout.

Figure 1:
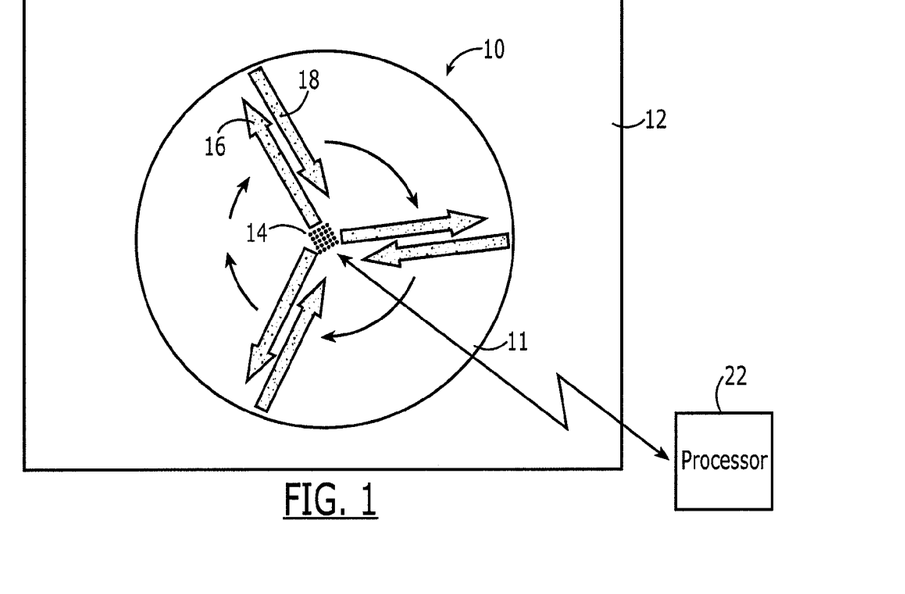
FIG. 1 is an illustration of a patch in accordance with one embodiment of the present disclosure.

Referring now to FIG. 1, a patch 10 is disclosed, such as a patch that may at least temporarily serve to repair a structure 12. In this regard, a patch may be placed on the structure so as to overly a structural anomaly that has been identified in the structure. The structure may include various types of structural anomalies including, for example, an anomaly in the repair patch material, an anomaly at the repair-structure interface, or in the structure beneath or adjacent to the repair patch. In one embodiment, the patch 10 may be applied to a structure 12 so as to overlie a structural anomaly, thereby at least temporarily repairing the structure until such time that the structure may be taken offline for a more extensive and permanent repair. The patch of this embodiment may be utilized in conjunction with a variety of different structures, including buildings, vehicles, such as aircraft, trains, ships and the like, machined forgings, castings, composite panels or other parts. In addition to its varied applications, the structure may be formed of various materials, such as metals, composites or combinations thereof.

The patch 10 generally includes a sheet 11 of material. While shown as having a circular shape, the sheet of material may have any shape and size that is desired. The sheet of material may be formed of a composite material. For example, the sheet of material may be a pre-cured composite material, such as a graphite-epoxy material, that is attached to the underlying structure 12. In this regard, the sheet of material may be formed of a plurality of layers of composite material that are integrated to form the resulting sheet. However, the sheet of material may be formed of other materials, such as metallic materials, such as aluminum, in other embodiments. Moreover, the sheet of material may be formed of the same or a different type of material as the underlying structure. The sheet of material may be flexible and pliable to allow the sheet to be manipulated to conform to a variety of surface contours, as well as to maintain intimate contact with the underlying structure. Moreover, the sheet of material may, alternatively, be rigid and provide support for the area of the structure that includes the structural anomaly. The sheet may be attached to the underlying structure in various manners, such as by means of an adhesive carried by the or otherwise applied to either the sheet or the structure.

The patch 10 also includes a frequency steerable array 14 carried by the sheet 11 of material. In this regard, the frequency steerable array may be mounted upon and carried by an outer surface of the sheet of material or an inner surface of the sheet of material relative to the structure 12. In other embodiments, the frequency steerable array may be disposed within the sheet of material. For example, the frequency steerable array may be embedded within a layer of the sheet of material so as not to be on the surface of the patch. In this embodiment, the layer of the sheet of material may serve as a waveguide to the structural waves. By being embedded within the sheet of material, the frequency steerable array may be embedded within a layer, between layers or above, below or within a repair bondline, such as the bondline formed by the adhesive that adheres the patch of one embodiment to the structure. While the frequency steerable array may be located at various positions upon the sheet of material, the frequency steerable array of one embodiment is located within a central portion of the sheet of material as shown in FIG. 1. A frequency steerable array includes a plurality of sources that are responsive to an input in order to emit structural waves, such as Lamb waves, that interfere with one another in such a manner that the combined beam of structural waves from the plurality of sources propagates in a particular direction. By altering the frequency of the input that drives the sources of a frequency steerable array to emit structural waves, the direction in which the combined beam of structural waves propagates may be controlled. As such, the structural waves emitted by the plurality of sources may be controllably steered relative to the sheet of material that carries the frequency steerable array and, thus, relative to the underlying structure. In one embodiment, for example, the frequency of the input that drives the sources of the frequency steerable array may be swept through a predefined range that serves to correspondingly scan the combined beam of structural waves emitted by the plurality of sources of the frequency steerable array through a predefined angular range, such as 360 degrees. See, for example, M. Romanoni, et al., "Two-Dimensional Periodic Actuators for Frequency-Based Beam Steering", Health Monitoring of Structural Biological Systems 2009, edited by Tribikran Kundu, Proc. of SPIE Vol. 7295, 729526.

The frequency steerable array 14 may include a single steerable beam transducer that, in turn, includes a plurality of piezo-electric or other type of transceivers that serve as the plurality of sources of the structural waves and that are responsive to the frequency of an input signal in terms of the actuation of the sources and direction of the resulting structural waves. Alternatively, the frequency steerable array may include a plurality of steerable beam transducers that may be utilized to provide the plurality of sources. In order to provide the input to the sources of the frequency steerable array, the patch 10 may include wires or other current paths to the respective sources and, in some embodiments, may also include a multiplexor or other hardware for controllably communicating with the respective sources. By utilizing a frequency steerable array to provide structural waves that may be controllably steered in various directions, however, the number of sensors may be reduced, along with reductions in the wiring or other current paths as well as the associated hardware required to communicate and interface with the frequency steerable array in comparison to at least some conventional designs. As such, the cost, complexity and weight of the patch may be advantageously reduced.

In one embodiment, the frequency steerable array 14 and/or the associated wiring may be directly written upon the sheet 11 of material. For example, the wiring is directly written upon the sheet of material and the frequency steerable array may then attached to the sheet of material, such as by deposition so as to be in electrical communication with the wiring. Alternatively, the frequency steerable array itself may be directly written upon the sheet of material. By directly writing the frequency steerable array and/or the associated wiring onto the sheet of material, the resulting profile may be maintained relatively small or low such that the surface of the structure may have advantageous aerodynamic properties.

Figure 2:
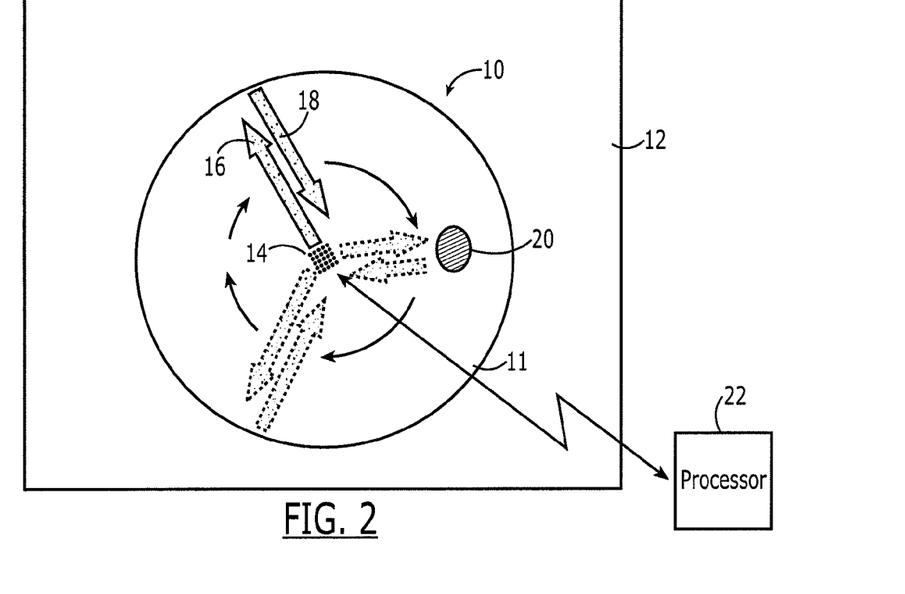
FIG. 2 is an illustration of the patch of FIG. 1 in which a structural anomaly has been detected in accordance with one embodiment of the present disclosures.

The frequency steerable array 14 not only emits the structural waves so as to propagate in a desired direction, but may also be configured to capture the structural waves that return following interaction with a structural anomaly 20. Structural anomaly 20 may be in the structure, or may be an anomaly due to the attachment of the patch 10 to the structure 20. For example, in the embodiment in which the frequency steerable array is comprised of a single steerable beam transducer having a plurality of piezo-electric transceivers, the piezo-electric transceivers may not only serve as sources of the structural waves, but may also serve to receive the returning signals. As shown in FIG. 1, for example, the structural waves 16 generated by the frequency steerable array may be steered completely about the patch 10 in 360 degrees. In the absence of a structural anomaly, the structural waves may be reflected from the edge of the patch as shown at 18 in FIG. 1 and may return to the frequency steerable array for collection and analysis. Alternatively, as shown in FIG. 2, a structural anomaly also would cause the structural waves to be reflected and to return to the frequency steerable array, albeit via a different and, in this illustrated embodiment, a shorter path.

The structural waves 18 returning to the frequency steerable array 14 may be captured as described above and may then be analyzed. In this regard, the patch 10 may include a processor or other computing device (hereinafter generally referenced as a "processor") for analyzing the returning structural waves. Alternatively, as shown in FIGS. 1 and 2, the patch may provide a representation of the returning structural waves, such as information regarding the amplitude, the time and/or the phase of the returning structural waves, to a processor 22 that is off-board the patch, such as via a wired or wireless connection therebetween. Based upon the returning structural waves, such as the amplitude, time and phase of the returning structural waves, any structural anomaly between the patch and the underlying structure 12 or within that portion of the structure itself that underlies the patch may be identified by the processor. In one embodiment, for example, the processor may initially obtain a baseline measurement following application of the patch to the underlying structure. This baseline measurement is presumed to be based upon returning structural waves that have reflected from the edges of the sheet 11 of material as shown in FIG. 1 in the absence of any intervening structural anomaly or in the presence of a known structural anomaly of a known size and shape. Thereafter, the frequency steerable array 14 may repeatedly emit structural waves 16 and detect the returning structural waves that may then be analyzed by the processor. In this regard, the processor may compare the measurements of these subsequent returning structural waves to the baseline measurement with differences between the subsequent measurements and the baseline measurement being noted as being potentially indicative of a structural anomaly or a change in a preexisting structural anomaly. In this regard, changes in the amplitude, time and phase of the returning structural waves from those measured in conjunction with the baseline measurement may be indicative of a structural anomaly, such as shown in FIG. 2, or a change in a preexisting structural anomaly. For example, reflections of the structural waves from discrete damage will cause a change in the time required for the returning structural waves to return and will accordingly indicate the presence of an anomaly. Additionally, the velocity of the structural waves has been shown to correlate to the stiffness of the material through which the structural waves propagate. As such, non-discrete damage that reduces stiffness, such as micro-cracking or heat damage, may also be identified based upon changes in the velocity of propagation of the structural waves and, therefore, corresponding changes in the time of propagation of the structural waves such that the non-discrete damage may be identified prior to being sufficiently significant to be visible.

In instances in which a structural anomaly 20 is identified, the structure 12 may then be taken offline in a scheduled manner for removal of the patch 10 and repair or other maintenance activities to address the structural anomaly prior to being returned to service. By detecting the structural anomaly in the patch repair, however, the structural anomaly may be identified and addressed while the structural anomaly is small, and the patch repairs may be maintained. Additionally, by detecting the onset of a structural anomaly with the patch in accordance with embodiments of the present disclosure, the repairs or other maintenance activities may be performed on a scheduled basis so as to reduce the negative impact that the removal of the structure from service may otherwise occasion.

Figure 3:
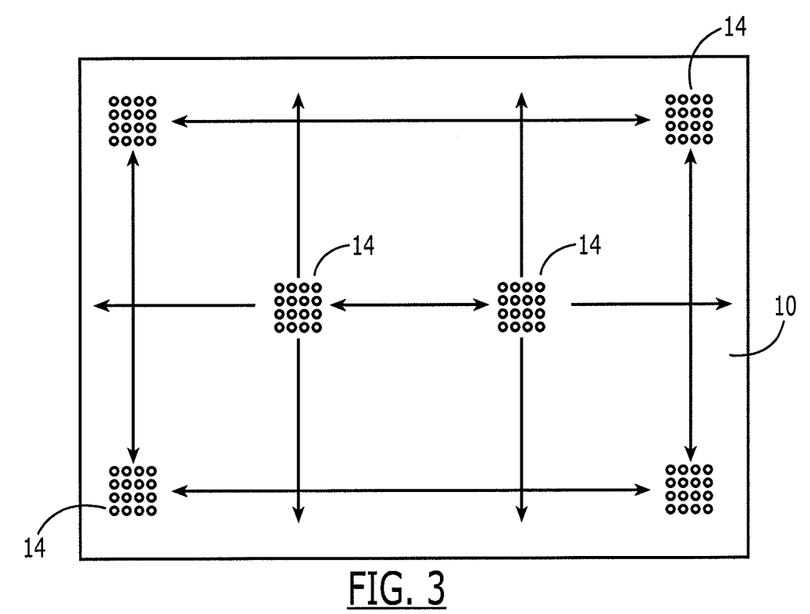
FIG. 3 is an illustration of a relatively large patch having a plurality of frequency steerable arrays positioned at respective locations for inspecting the structure in accordance with one embodiment of the present disclosure.

In other embodiments, relatively large patch repairs may include multiple frequency steerable arrays 14 configured to receive structural waves following propagation through a portion of the structural repair patch. The structural waves that are received may be analyzed in order to identify structural anomalies 20. As described above, and as shown in conjunction with the structural waves that are directed outward from the frequency steerable arrays that are disposed within the interior of the structural patch of the embodiment of FIG. 3, some of the frequency steerable arrays may be positioned relative to the structural patch such that a frequency steerable array emits structural waves 16 that subsequently return to the same frequency steerable array, such as following reflection from an edge of the patch. Alternatively, some of the frequency steerable arrays may be positioned such that the structural waves emitted by one frequency steerable array are received by another frequency steerable array. In the embodiment of FIG. 3, the structural waves that are emitted by one frequency steerable array and received by another frequency steerable array are shown by the lines having arrows at both ends. Regardless of the origin of the structural waves, the frequency steerable arrays may provide a representation of the structural waves that have been detected, such as the amplitude, time and phase of the structural waves, to a processor, either onboard or offboard of the structural patch, for analysis of the structural waves.

As before, a baseline measurement may be initially captured that defines the amplitude, time and phase of the structural waves that are received in the absence of structural anomalies or with a predefined, generally acceptable, degree of structural anomalies. Thereafter, the structural waves that are detected by the frequency steerable arrays 14 may be analyzed relative to the baseline measurement in order to detect a structural anomaly or the growth of a preexisting structural anomaly by changes in the returning structural waves, such as changes in the amplitude, time and phase of the structural waves received by one or more of the frequency steerable arrays. Based upon the analysis of the returning structural waves, any structural anomalies that are identified or any preexisting structural anomalies that are detected to have grown may cause appropriate repair or maintenance activities to be scheduled for the structure 12.

Figure 4:
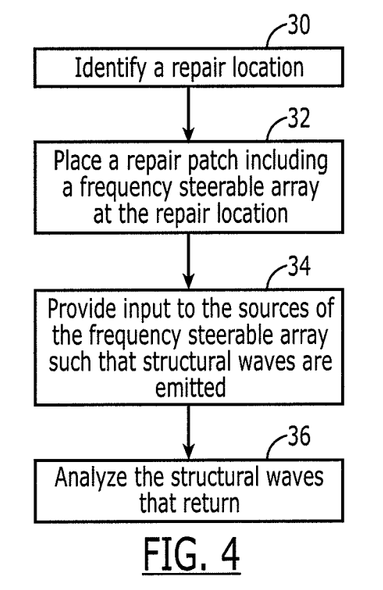
FIG. 4 is a flowchart illustrating operations performed during monitoring of a patch repair in accordance with one embodiment of the present disclosure.
Figure 5:
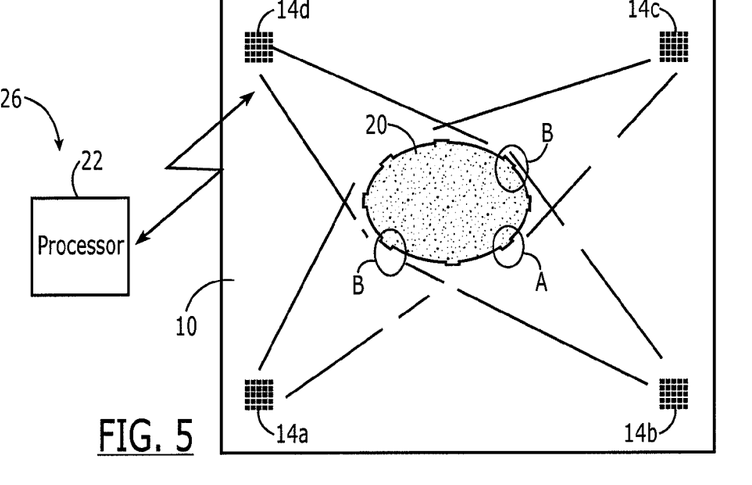
FIG. 5 is an illustration of a structural patch repair on which a plurality of frequency steerable arrays are positioned in order to identify a characteristic, such as the size and shape, of a structural repair in accordance with one embodiment of the present disclosure.

In one embodiment depicted in FIGS. 4 and 5, the returning structural waves 18 may be analyzed in order to identify a characteristic of a structural anomaly 20. As shown in operation 30 of FIG. 4, a repair location may initially be identified. The repair location may be identified in various manners including by visual inspection of the structure by a technician, by various non-destructive evaluation or inspection techniques or the like in order to identify a structural anomaly. Once identified, a patch repair with at least one frequency steerable array 14 may be placed upon the structure 12 over the structural anomaly. See operation 32 of FIG. 4. As before, the frequency steerable array may include a plurality of sources for emitting structural arrays in response to an input having a variable frequency. As shown in operation 34 of FIG. 4, input to the sources of the frequency steerable array may then be provided such that the structural waves 16 emitted by the plurality of sources are controllably steered so to interact with the structural anomaly. The structural waves 18 returning following interaction with the structural anomaly may then be analyzed, such as by a processor 22, to identify a characteristic of the structural anomaly. For example, the returning structural waves may be analyzed to identify changes in the structural anomaly, such as growth of the structural anomaly. Any changes in the structural anomaly may therefore be identified in a timely manner such that appropriate repairs or other maintenance activities may be undertaken while such repairs or maintenance activities are relative small and inexpensive. While the method of this embodiment may be employed with respect of variety of structures, the method of this embodiment may be particularly advantageous in conjunction with the monitoring of structural anomaly in areas having limited access, limited visibility or the like.

As shown in FIG. 5, a plurality of frequency steerable arrays 14 may be positioned about a structural patch 10 that overlies an anomaly 20 that has been identified and is being monitored. The structural waves 16 emitted by each frequency steerable array may be controllably directed, such as by means of the frequency of the input provided to the sources of the respective frequency steerable array, so as to sweep across the portion of the structure 12 in which the structural anomaly is positioned. Some of the structural waves will be reflected from the structural anomaly and return to the frequency steerable array that originally emitted the structural waves. However, other structural waves will be reflected from the structural anomaly and directed to another frequency steerable array that is different than the frequency steerable array that originally emitted the structural waves. For example, those structural waves emitted by the frequency steerable array designated 14b in FIG. 5 will be reflected from that portion of the structural anomaly that is circled and labeled A so as to return to the same frequency steerable array 14b. However, the structural waves emitted by frequency steerable array 14b that reflect from those portions of the structural anomaly that are circled and labeled B will reflect to other frequency steerable arrays, such as frequency steerable arrays 14a and 14c in the embodiment of FIG. 5. Based upon the structural waves that are received by each of the frequency steerable arrays including the identification of whether the structural waves that are received originated with the same frequency steerable array or another frequency steerable array, the analysis of the structural waves may permit the size and shape of the structural anomaly to be determined as a result of the reflection of the structural waves from the various edges of the structural anomaly.

In one embodiment, the frequency steerable arrays 14 operate under the control of an ultrasonic pulser/receiver system 26 having a processor 22 having or controlling a multiplexor card or configured to execute a corresponding software program for selecting the individual steerable array to be pulsed. As such, the source of the structural waves and the time at which the structural waves were emitted are known, thereby permitting the returning structural waves to be identified as having been emitted by a respective frequency steerable array at a particular time. As such, the processor can determine the path traveled and the time elapsed between emission and reception of the structural waves.

Once the patch 10 has been positioned over the anomaly 20 with the frequency steerable arrays 14 positioned about the anomaly, the operator may provide the processor 22 with information defining the positions of the frequency steerable arrays based upon distance measurements between the anomaly and the various frequency steerable arrays. Alternatively, once the frequency steerable arrays have been positioned about the anomaly and assuming that the velocity of the structural waves through the structure 12 is known and that those portions of the structure between the adjacent frequency steerable arrays are free of anomalies, the frequency steerable arrays may be scanned, either fully or partially, and the structural waves that are received by another frequency steerable array may be analyzed in order to determine the position of each frequency steerable array. The position of each frequency steerable array may then be provided to and utilized by the processor in subsequently characterizing the anomaly in the process described above.

Figure 6:
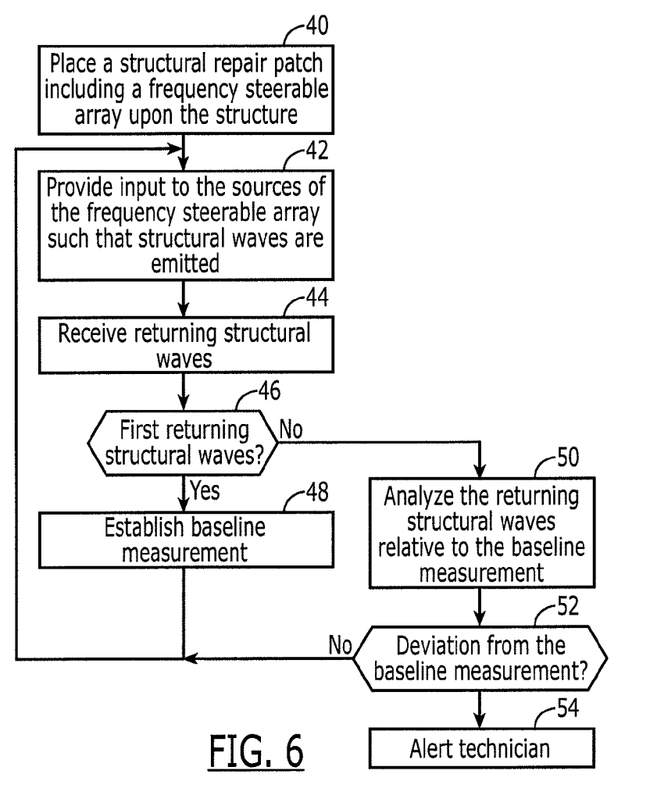
FIG. 6 is a flowchart illustrating operations performed during monitoring of a relatively large structural patch repair in accordance with another embodiment of the present disclosure.

As shown in FIG. 6, the method of one embodiment analyzes the returning structural waves 18 by comparing the returning structural waves to a baseline measurement. In this embodiment, after placing the patch repair and its frequency steerable array 14 upon the structure 12, providing input to the sources of the frequency steerable array such that structural waves 16 are emitted and receiving the returning structural waves, it may be determined as to whether the returning structural waves constitute the first measurement following the placement of the patch with the frequency steerable array upon the structure. See operations 40, 42, 44 and 46 of FIG. 6. If so, a baseline measurement may initially be captured. See operation 48. Thereafter, the returning structural waves may be analyzed to determine any differences relative to the baseline measurement, such as in terms of the amplitude, time or phase of the returning structural waves. See operations 50 and 52. In instances in which the returning structural waves deviate from the baseline measurement by more than a predefined threshold amount, a technician may be alerted as to a likely change in the structural anomaly 20 such that repair or other maintenance activities may take place or a more detailed inspection, such as a visual inspection or other non-destructive evaluation or inspection may be conducted. See operation 54 of FIG. 6.

Figure 7:
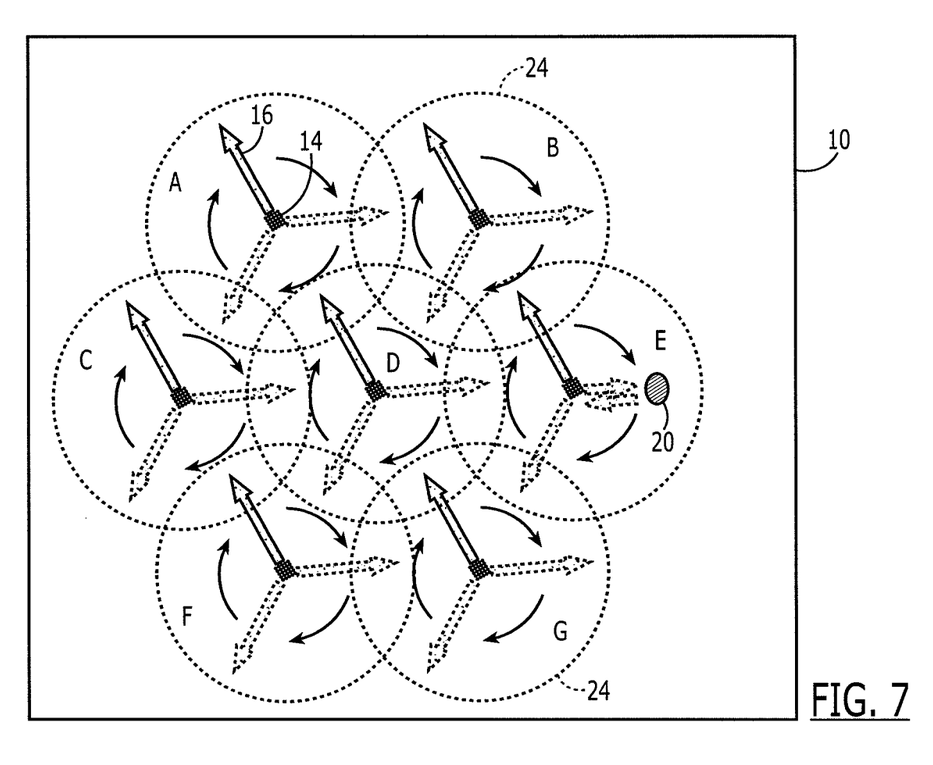
FIG. 7 is an illustration of the sequential positioning of a frequency steerable array at each of a plurality of locations upon a relatively large structural patch in order to inspect the structure in accordance with one embodiment of the present disclosure.

In another embodiment, frequency steerable arrays 14 may be utilized in order to inspect a relatively large patch 10. As shown at location A in FIG. 7, a frequency steerable array may be positioned at a respective location upon the patch and the sources of the frequency steerable array may then be driven by inputs having a frequency that is swept through a predefined range in order to correspondingly sweep the structural waves 16 emitted by the frequency steerable array through a predefined angular range, such as 360° in the illustrated embodiment. The returning structural waves 18 may be detected by the frequency steerable array and then analyzed, such as by processor 22, in order to identify a structural anomaly 20, if any, within the range of the frequency steerable array. The frequency steerable array may then be sequentially positioned at each of a plurality of locations as illustrated by locations A, B, C, D, E, F and G in FIG. 7 and the inspection process repeated. While the pattern via which the frequency steerable arrays are positioned on the patch may vary depending upon the structure and the intent of the inspection, the frequency steerable arrays of one embodiment are positioned in accordance with a grid pattern in order to comprehensively inspect the structure in an efficient manner. In addition, the spacing between respective locations at which the frequency steerable array is positioned upon the structure may also vary depending upon the effective inspection range of the frequency steerable array (shown in the embodiment of FIG. 7 by the dashed lines 24). As shown in FIG. 7, the spacing between respective locations at which the frequency steerable arrays are located is chosen in one advantageous embodiment such that the effective inspection range at one location overlaps somewhat with the effective inspection ranges at the neighboring locations such that the entire patch repair is inspected with no regions existing between the effective inspection ranges that are not inspected. Even with an overlap between the effective inspection ranges of neighboring locations, the method of this embodiment facilitates a relatively rapid inspection of a large patch repair.

In an instance in which a structural anomaly 20 is detected by analysis of the returning structural waves 18, the method of this embodiment may alert a technician of the structural anomaly and the relative location of the structural anomaly, based upon the location of the frequency steerable array 14 at the time that the structural anomaly was identified. For example, the processor 22 may issue an alert identifying the approximate location of a potential structural anomaly.

Many modifications and other embodiments of the present disclosure set forth herein will come to mind to one skilled in the art to which these embodiments pertain having the benefit of the teachings presented in the foregoing descriptions and the associated drawings. Therefore, it is to be understood that the present disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A patch for monitoring a structure for a structural anomaly, the method comprising:
   a sheet of material configured to be attached to the structure; and
   a frequency steerable array carried by said sheet of material, said frequency steerable array comprising a plurality of sources for emitting structural waves in response to an input having a variable frequency such that variations in the frequency of the input cause a direction in which the structural waves emitted by the plurality of sources propagate to be controllably steered relative to said sheet of material, wherein said frequency steerable array is configured to be responsive to the frequency of the input being swept through a predefined range so as to correspondingly scan the structural waves through a predefined range of angles relative to said sheet of material, and wherein said frequency steerable array is configured to capture the structural waves returning following interaction with the structural anomaly; and
   a processor configured to communicate with the frequency steerable array so as: (i) to confirm an absence of the structural anomaly in an instance in which the structural waves are reflected from an edge of the sheet of material and return to the frequency steerable array and (ii) to detect the structural anomaly in an instance in which the structural anomaly is present and the structural waves are reflected from the structural anomaly in the structure underlying the sheet of material at a location between the frequency steerable array and the edge of the sheet of material and return to the frequency steerable array before a reflection from the edge of the sheet of material.

2. A patch according to claim 1 wherein said frequency steerable array is carried by a central portion of said sheet of material.

3. A patch according to claim 1 wherein said frequency steerable array comprises a single steerable beam transducer comprising a plurality of piezo-electric transceivers.

4. A patch according to claim 1 wherein said frequency steerable array is configured such that the structural waves are controllably steered in 360° about said sheet of material.

5. A patch according to claim 1 wherein said frequency steerable array is embedded within the sheet of material, and wherein the sheet of material is configured to guide the structural waves emitted by the frequency steerable array.

6. An assembly for monitoring a structure for a structural anomaly, the assembly comprising:
   a sheet of material configured to be attached to the structure;
   one or more frequency steerable arrays configured to be carried by the sheet of material, each frequency steerable array comprising a plurality of sources for emitting structural waves in response to an input having a variable frequency such that variations in the frequency of the input cause a direction in which the structural waves emitted by the plurality of sources propagate to be controllably steered relative to the structure, wherein at least one frequency steerable array is configured to be responsive to the frequency of the input being swept through a predefined range so as to correspondingly scan the structural waves through a predefined range of angles relative to said sheet of material; and
   a processor configured to communicate with the one or more frequency steerable arrays for analyzing a representation of the structural waves that return to the one or more frequency steerable arrays following interaction with the structure in order to identify the structural anomaly, wherein, following emission of structural waves by a respective frequency steerable array of the one or more frequency steerable arrays, the processor is configured: (i) to confirm an absence of the structural anomaly in an instance in which the structural waves are reflected from an edge of the sheet of material and return to the respective frequency steerable array and (ii) to detect the structural anomaly in an instance in which the structural anomaly is present and the structural waves are reflected from the structural anomaly in the structure underlying the sheet of material at a location between the respective frequency steerable array and the edge of the sheet of material and return to the respective frequency steerable array before a reflection from the edge of the sheet of material.

7. An assembly according to claim 6 wherein said processor is configured to analyze a representation of the structural waves that return to the frequency steerable arrays to identify a characteristic of the structural anomaly.

8. An assembly according to claim 7 wherein the processor is configured to analyze a representation of the structural waves that return to the frequency steerable arrays to identify a size or shape of the structural anomaly.

9. An assembly according to claim 6 wherein each frequency steerable array is configured to capture the structural waves returning following interaction with the structural anomaly.

10. An assembly according to claim 6 wherein each frequency steerable array comprises a single steerable beam transducer comprising a plurality of piezo-electric transceivers.

11. An assembly according to claim 6 wherein each frequency steerable array is configured such that the structural waves are controllably steered in 360° about said sheet of material.

12. An assembly according to claim 6 wherein the plurality of frequency steerable arrays are embedded within the sheet of material, and wherein the sheet of material is configured to guide the structural waves emitted by the frequency steerable array.

13. A method of monitoring a patch-repaired structure for a structural anomaly, the method comprising:
   identifying the structural anomaly;
   placing a patch repair with at least one frequency steerable array upon the structure, said frequency steerable array comprising a plurality of sources for emitting structural waves in response to an input having a variable frequency with a direction in which the structural waves propagate being dependent upon the frequency of the input;
   providing the input to the sources of the frequency steerable array such that the structural waves emitted by the plurality of sources are controllably steered so as to interact with the structural anomaly, wherein providing the input comprises sweeping the frequency of the input through a predefined range so as to correspondingly scan the structural waves through a predefined range of angles relative to the structure; and
   analyzing the structural waves returning following interaction with the structural anomaly to identify a characteristic of the structural anomaly, wherein analyzing the structural waves comprises: (i) confirming an absence of the structural anomaly in an instance in which the structural waves are reflected from an edge of the patch repair and return to the frequency steerable array and (ii) detecting the structural anomaly in an instance in which the structural anomaly is present and the structural waves are reflected from the structural anomaly in the structure underlying the sheet of material at a location between the frequency steerable array and the edge of the sheet of material and return to the frequency steerable array before a reflection from the edge of the sheet of material.

14. A method according to claim 13 wherein analyzing the structural waves comprises initially capturing a baseline measurement, and wherein providing the input comprises repeatedly providing the input to the sources over time and repeatedly analyzing the structural waves returning following interaction with the structural anomaly in order to identify structural waves that deviate from the baseline measurement.

15. A method according to claim 13 wherein analyzing the structural waves comprises analyzing amplitude, time and phase of the structural waves returning following interaction with the structural anomaly.

16. A method according to claim 13 wherein placing the patch repair having at least one frequency steerable array upon the patch-repaired structure comprises placing the patch repair having a plurality of frequency steerable arrays on the structure so as to overlie the structural anomaly, and wherein analyzing the structural waves comprises analyzing the structural waves returning to each of the plurality of frequency steerable arrays to identify a size or shape of the structural anomaly.

17. A method according to claim 16 wherein providing the input comprises providing the input to the sources of each of the frequency steerable arrays such that some structural waves are reflected from the structural anomaly and return to the frequency steerable array that emitted the structural waves and other structural waves are reflected from the structural anomaly and are directed to another frequency steerable array, different than the frequency steerable array that emitted the structural waves.

18. A method according to claim 13 further comprising fabricating the patch repair by providing a sheet of material, directly writing wiring upon the sheet of material and attaching the frequency steerable array upon the sheet of material so as to be in electrical communication with the wiring.

19. A method according to claim 13 further comprising fabricating the patch repair by providing a sheet of material and directly writing the frequency steerable array upon the sheet of material.

* * * * *